(12) United States Patent
Mizuno et al.

(10) Patent No.: US 8,540,393 B2
(45) Date of Patent: Sep. 24, 2013

(54) FIRST AND SECOND LIGHT-EMITTING ELEMENTS HAVING IDENTICAL PEAK EMISSION INTENSITIES

(75) Inventors: Kyosuke Mizuno, Hachioji (JP); Shinji Yamashita, Tachikawa (JP); Masato Toda, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 11/890,578

(22) Filed: Aug. 7, 2007

(65) Prior Publication Data

US 2008/0037247 A1  Feb. 14, 2008

(30) Foreign Application Priority Data

Aug. 9, 2006  (JP) ................................ 2006-217510

(51) Int. Cl.
*A61B 1/06* (2006.01)
(52) U.S. Cl.
USPC .......................................... 362/231; 362/574
(58) Field of Classification Search
USPC ... 362/231, 555, 574; 348/68; 600/128–180; 385/117
See application file for complete search history.

(56) References Cited

U.S. PATENT DOCUMENTS

| | | | | |
|---|---|---|---|---|
| 6,002,424 A * | 12/1999 | Rapa et al. | ....................... | 348/66 |
| 6,106,457 A * | 8/2000 | Perkins et al. | ................. | 600/175 |
| 6,260,994 B1 * | 7/2001 | Matsumoto et al. | .......... | 362/574 |
| 6,438,302 B1 * | 8/2002 | Utsui et al. | ..................... | 385/117 |
| 6,449,006 B1 * | 9/2002 | Shipp | .............................. | 348/70 |
| 6,587,711 B1 * | 7/2003 | Alfano et al. | .................. | 600/476 |
| 6,857,762 B2 * | 2/2005 | Shimokawa et al. | ......... | 362/245 |
| 6,918,693 B2 * | 7/2005 | Ota et al. | ....................... | 362/574 |
| 7,152,996 B2 * | 12/2006 | Luk | ................................ | 362/240 |
| 7,177,033 B2 * | 2/2007 | Yoshida | ......................... | 356/601 |
| 7,347,817 B2 * | 3/2008 | Glukhovsky et al. | ......... | 600/181 |
| 7,469,160 B2 * | 12/2008 | Banks et al. | ................... | 600/476 |
| 7,530,948 B2 * | 5/2009 | Seibel et al. | ................... | 600/178 |
| 7,585,274 B2 * | 9/2009 | Homma | ......................... | 600/160 |
| 2003/0035048 A1 * | 2/2003 | Shipp | ............................... | 348/68 |
| 2006/0215406 A1 * | 9/2006 | Thrailkill | ...................... | 362/252 |
| 2006/0217594 A1 * | 9/2006 | Ferguson | ...................... | 600/175 |

FOREIGN PATENT DOCUMENTS

| | | |
|---|---|---|
| JP | 63-260526 | 10/1988 |
| JP | 07-275200 | * 4/1994 |
| JP | 11-225953 | 8/1999 |
| JP | 11-253398 | 9/1999 |
| JP | 2005-74034 | 3/2004 |
| JP | 2005-168520 | 6/2005 |
| JP | 2006-122335 | 5/2006 |

OTHER PUBLICATIONS

English machine translation of JP 07-275200.*

(Continued)

*Primary Examiner* — Jong-Suk (James) Lee
*Assistant Examiner* — Leah S Macchiarolo
(74) *Attorney, Agent, or Firm* — Scully, Scott, Murphy & Presser, P.C.

(57) ABSTRACT

A light source apparatus includes a first light-emitting element to generate an illumination light with a first light emission intensity to be applied to a subject, and a second light-emitting element to generate an illumination light with a second light emission intensity, including at least light with a wavelength different from the illumination light generated from the first light-emitting element. The first light-emitting element and second light-emitting element are arranged, so that the peaks of the first emission intensity and second emission intensity become identical.

6 Claims, 7 Drawing Sheets

(56) References Cited

OTHER PUBLICATIONS

Japanese Official Action mailed Sep. 13, 2011 in corresponding Japanese Patent Application No. 2006-217510, together with English language translation.

Japanese Final Office Action dated Oct. 2, 2012 together with an English Language Translation of corresponding Patent Application No. JP 2006-217510.

* cited by examiner

FIRST AND SECOND LIGHT-EMITTING ELEMENTS HAVING IDENTICAL PEAK EMISSION INTENSITIES

CROSS-REFERENCE TO RELATED APPLICATIONS

This application is based upon and claims the benefit of priority from prior Japanese Patent Application No. 2006-217510, filed Aug. 9, 2006, the entire contents of which are incorporated herein by reference.

BACKGROUND OF THE INVENTION

1. Field of the Invention

The present invention relates to a light source apparatus having a plurality of light-emitting elements to emit light with a plurality of different wavelengths.

2. Description of the Related Art

Jpn. Pat. Appln. KOKAI Publication No. 11-225953 discloses an electronic endoscope, which is provided with an image pickup means for observation and red (R), green (G) and blue (B) light-emitting elements in the distal end portion of an insertion part.

BRIEF SUMMARY OF THE INVENTION

According to a first aspect of the invention, there is provided a light source apparatus comprising a first light-emitting element to generate an illumination light with a first light emission intensity to be applied to a subject, and a second light-emitting element to generate an illumination light with a second light emission intensity, including at least light with a wavelength different from the illumination light generated from the first light-emitting element, wherein the first light-emitting element and second light-emitting element are arranged, so that peaks of the first emission intensity and second emission intensity become identical.

According to a second aspect of the invention, there is provided a light source apparatus comprising a first light-emitting element to generate an illumination light with a first light emission intensity to be applied to a subject, and a second light-emitting element to generate an illumination light with a second light emission intensity, having a wavelength different from the illumination light generated from the first light-emitting element, wherein at least one of the first light-emitting element and second light-emitting element is arranged to be two or more in number, and the first light-emitting element and second light-emitting element are arranged, so that peaks of the first light emission intensity and second light emission intensity become identical.

According to a third aspect of the invention, there is provided a light source apparatus wherein the first light-emitting element and second light-emitting element are arranged, so that peaks of the first emission intensity and second emission intensity coincide with the center of an image pickup element to image a subject.

According to a fourth aspect of the invention, there is provided a light source apparatus comprising a first light-emitting element to generate an illumination light with a first light emission intensity to be applied to a subject, a second light-emitting element to generate an illumination light with a second light emission intensity, having a wavelength different from the illumination light generated from the first light-emitting element, and a control means to control the light emission amount of the first light-emitting element and second light-emitting element, so that the peak of the first emission light intensity and peak of the second emission light intensity becomes identical, wherein at least one of the first light-emitting element and second light-emitting element is arranged to be two or more in number.

According to a fifth aspect of the invention, there is provided a light source apparatus comprising a first light-emitting element to generate an illumination light with a first light emission intensity to be applied to a subject, a second light-emitting element to generate an illumination light with a second light emission intensity, having a wavelength different from the illumination light generated from the first light-emitting element, and a control means to control the light emission amount of the first light-emitting element and second light-emitting element, so that the peak of the first emission light intensity and peak of the second emission light intensity becomes identical, wherein at least one of the first light-emitting element and second light-emitting element is arranged to be two or more in number, and the light emission amount of these light-emitting elements are independently controlled.

Objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Hereinafter, embodiments of the invention will be explained in detail with reference to the accompanying drawings.

Figure 1:
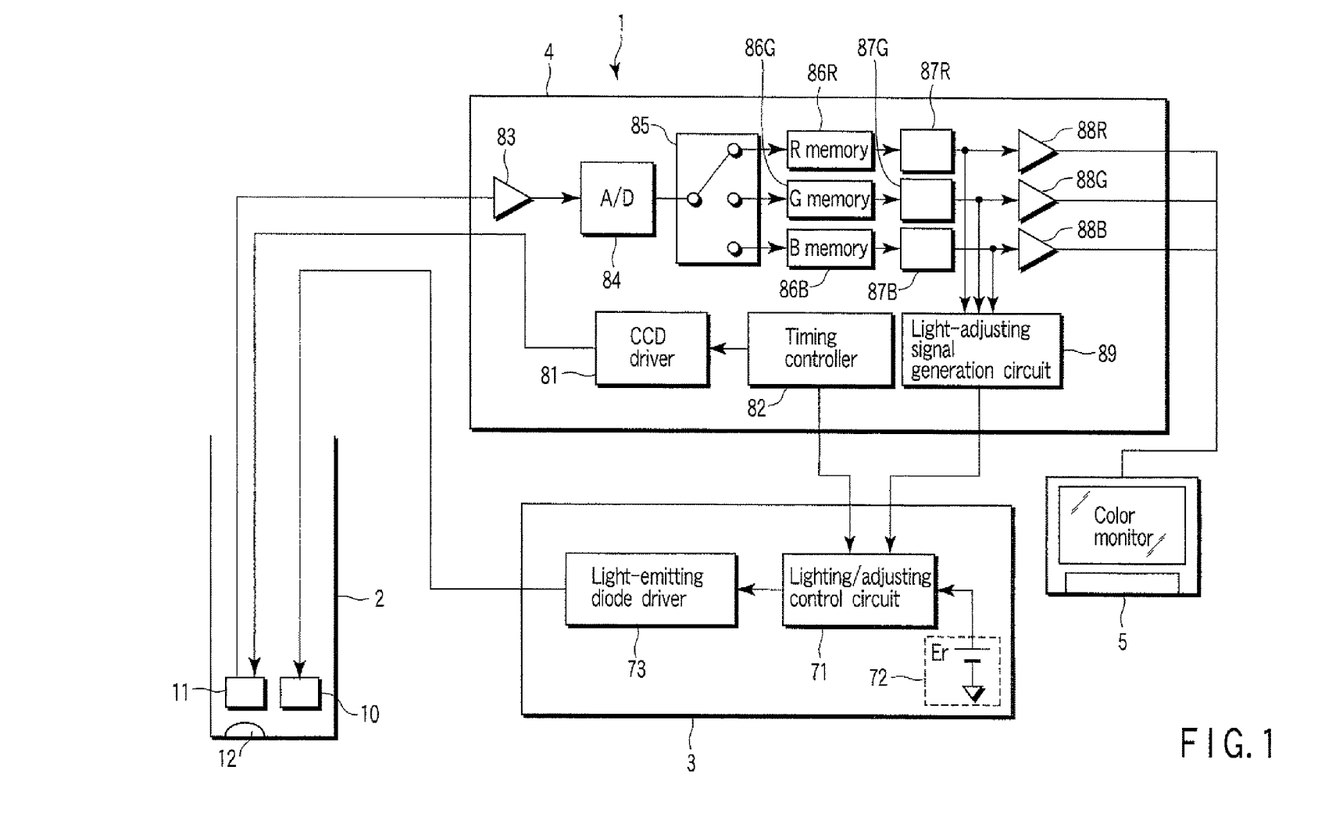
FIG. 1 is a block diagram of a field-sequential endoscope apparatus 1 according to an embodiment of the present invention.

Hereinafter, embodiments of the invention will be explained in detail with reference to the accompanying drawings. FIG. 1 shows a configuration of a field-sequential endoscope apparatus 1 according to an embodiment of the invention. The endoscope apparatus 1 comprises an electronic endoscope 2 having a light-emitting diode 10, a light-emitting diode driving controller 3 to control driving of the light-emitting diode 10, a video processor 4 as a signal processor to process image signals obtained by the electronic endoscope 2, and a color monitor 5 to display image signals processed by the video processor 4. The electronic endoscope 2, light-emitting diode driving controller 3, video processor 4 and color monitor 5 are connected through a signal line. Only one light-emitting diode 10 is shown in FIG. 1, but actually, three diodes are arranged (for red, green and blue).

In the above configuration, when a subject (not shown) is illuminated by lighting the diode 10, an optical image of the illuminated subject is formed on the CCD 11 arranged on the focal plane of the electronic endoscope 2 through objective optics 12. The optical image is photoelectrically converted by the CCD 11, and stored as an electric charge.

When the CCD driving signal is applied to the corresponding CCD 11 from a CCD driver 81 in the video processor 4, the electric charge stored in the CCD 11 is output to the outside as an image pickup signal output.

The output signal of the CCD 11 is amplified by a preamplifier 83 in the video processor 4, and digitized by an analog-to-digital converter 84. The converted digital R/G/B image pickup signals are stored in R/G/B memories 86R, 86G and 86B by changing a selector 85 in synchronization with the field-sequential illumination.

The pickup signals stored in the R/G/B memories 86R, 86G and 86B are simultaneously read, and converted to analog R/C/B signals by digital-to-analog converters 87R, 87G and 97B. These R/G/B signals are output to the color monitor 5 together with a not-shown synchronizing signal through buffers 88R, 88G and 88B, and a subject image is displayed in color on its display surface.

The R/G/B signals output through the digital-to-analog converters 86R, 87G and 87B are applied to a light-adjusting signal generator circuit 89, to generate a light-adjusting signal integrated for one field period, for example. The light-adjusting signal is applied to a lighting/adjusting control circuit 71 of the light-emitting diode driving controller 3.

The lighting/adjusting controller 71 is supplied with a reference voltage Er from a level generation circuit 72, which generates a reference level corresponding to brightness suitable for observation. The reference level can be varied. The lighting/adjusting controller 71 generates a difference signal by comparing the reference voltage Er with the light-adjusting signal, and varies the light-emitting intensity and period of the light-emitting diode 10 by supplying a light-emitting diode driver 73 with lighting/adjusting signals where the difference signal is zero.

Figure 2:
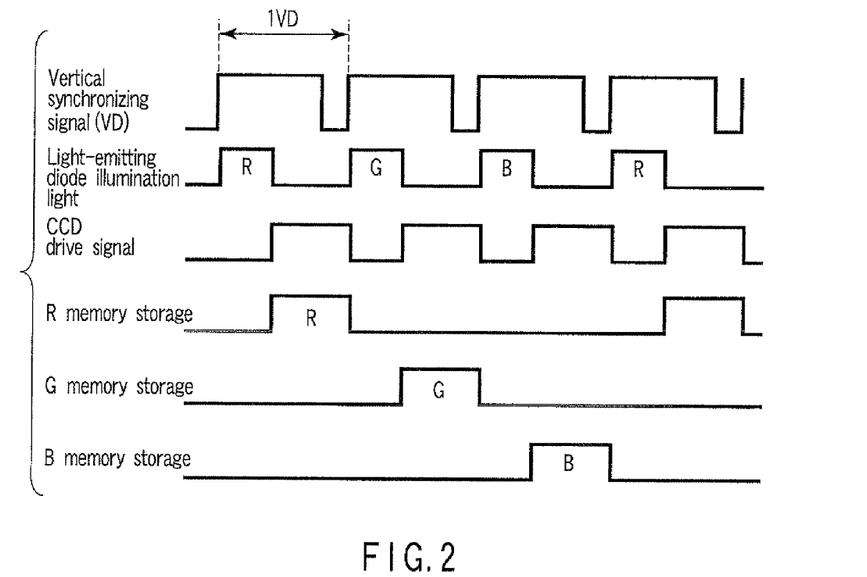
FIG. 2 is a timing chart showing the timing relationship between operations of lighting a light-emitting diode 10, driving a CCD 11 and storing an image pickup signal.

FIG. 2 is a timing chart showing the timing relationship between operations of lighting the light-emitting diode 10, driving the CCD 11 and storing an image pickup signal. A timing controller 82 is driven by a vertical synchronizing signal (VD) generated in a not-shown synchronizing signal generation circuit. The operation timing of the CCD driver 81 and lighting/adjusting control circuit 71 are determined by the output signal from the timing controller 82.

Namely, the lighting/adjusting controller 71 outputs a light-emitting diode driving signal to the light-emitting diode driver 73, in synchronization with the output signal from the timing controller 82. The light-emitting diode driver 73 drives the light-emitting diode 10 in the order of R, G and B, in synchronization with the light-emitting diode driving signal. The lighting/adjusting control of the light-emitting diode 10 is performed based on the reference voltage generated by the reference level generation circuit 72.

The CCD driver 81 outputs a CCD driving signal to the CCD 11, in synchronization with the output signal from the timing controller 82, after the R/G/B light emitting period. Therefore, the CCD 11 is driven, and image pickup operation is performed. Image pickup signals obtained by the image pickup operation are stored in the R/G/B memories 86R, 86G and 86B according to the switching of the selector 85. The above-mentioned lighting of the R/G/B light-emitting diode 10, driving the CCD 11 and storing the image pickup signals are performed within one VD period indicating a partition between two screens.

As shown in FIG. 1, the CCD 11 as an image pickup element and light-emitting diode 10 as a light source are arranged in the distal end of the electronic endoscope 2. When arranging these elements in the distal end portion having a thin diameter, there is a problem that uneven color occurs in an endoscopic image depending on the arrangement. Hereinafter, how to arrange the R/G/B light-emitting diode 10 for the CCD 11 will be studied.

Embodiment 1

Figure 3:
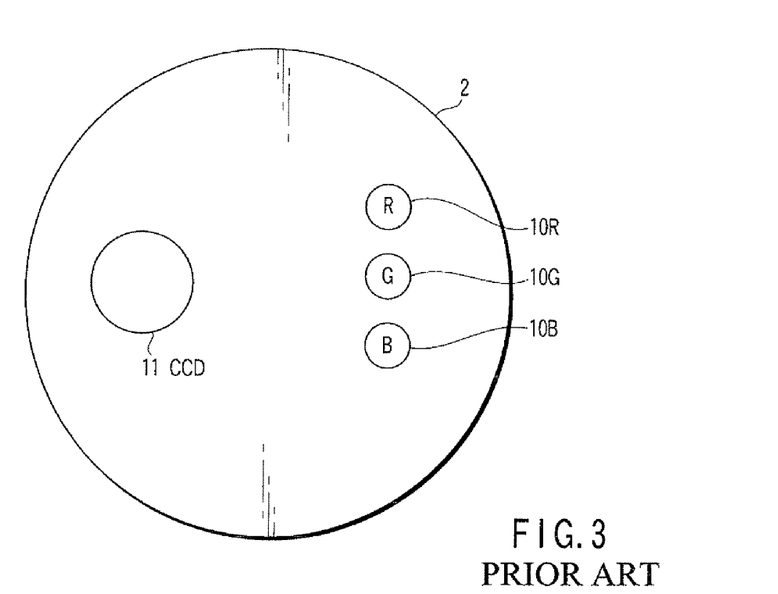
FIG. 3 is a view for explaining a problem in conventional arrangement, in the first embodiment of the invention.

In the first embodiment of the invention, a CCD is arranged at a position displaced from the center of a distal end portion of an endoscope. FIG. 3 is a view for explaining a problem in conventional arrangement. Light-emitting diodes 10R, 10G and 10B are arranged in one vertical line. The R, G and B light-emitting diodes 10R, 10G and 10B are not arranged considering the luminous intensity distribution of the R/G/B light-emitting diodes 10R, 10G and 10B. When the light-emitting diodes 10R, 10G and 10B are lit in this arrangement, the light-emitting points of the light-emitting diodes 10R, 10G and 10B are different in the angle of view of CCD 11, and the luminous intensity distribution of the light-emitting diodes 10R, 10G and 10B are different, and the illumination peak positions of the light-emitting diodes 10R, 10G and 10B are displaced, causing uneven color in endoscopic images.

Figure 4:
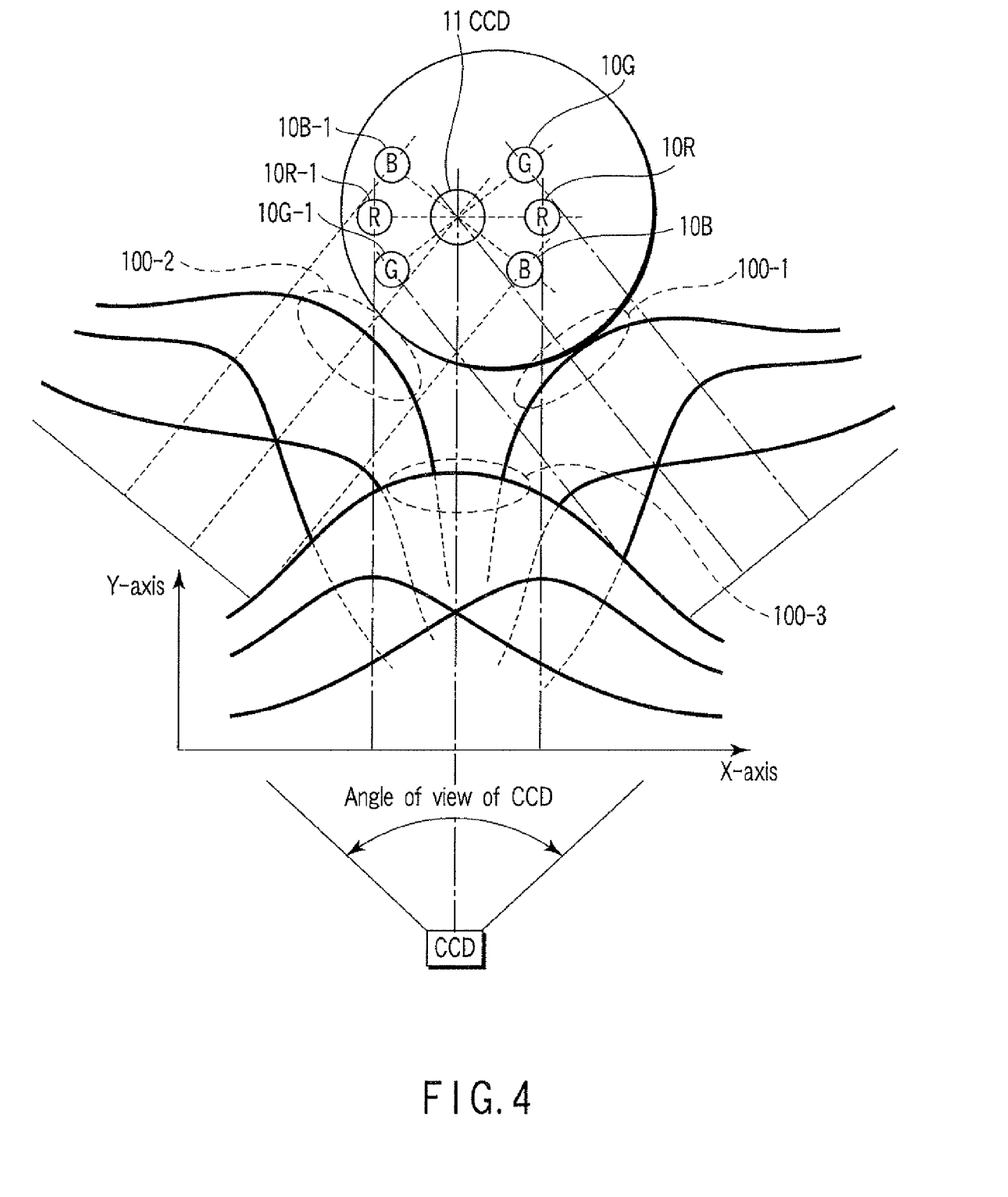
FIG. 4 is a view showing arrangement in a distal end portion of an endoscope according to a first embodiment of the invention, and illuminance on a plane separated by a predetermined distance from each light-emitting element.

FIG. 4 shows the arrangement in the distal end portion of an endoscope according to the first embodiment, and the illuminance (in the vertical [Y-axis] direction in the drawing) on the plane separated by a predetermined distance from the endoscope distal end. The horizontal (X-axis) direction in the drawing indicates the distance on the vertical line passing through the center of two light-emitting elements of the same kind. In FIG. 4, the portions with high illuminance lit by the light with R/G/B wavelengths are called light emission intensity peak portions 100-3, 100-1 and 100-2, respectively. These three light emission peak portions 100-3, 100-1 and 100-2 are on the optical axis of the CCD 11, and located at identical position.

Here, the R/G/B light-emitting diodes 10R and 10R-1, 10G and 10G-1, and 10B and 10B-1 are arranged so that the CCD 11 is put between them. Further, as the light-emitting diodes 10R, 10R-1 are arranged at the positions separated by the same distance from the CCD 11, the peaks of the light emission strengths are identical. This is the same as for the other color light-emitting diodes 10G and 10G-1, and 10B and 10B-1.

Here, two R/G/B light-emitting diodes are arranged, but it is allowed to arrange two or more one-color light-emitting diodes.

As described above, in arrangement of R/G/B light-emitting diodes, respective R/G/B light-emitting diodes are arranged in such a way that the CCD 11 is put between R, G, or B light-emitting diodes or the CCD 11 is surrounded by R, G, or B light-emitting diodes. Therefore, it is possible that the peak positions of the light-emitting diodes when viewed from the CCD 11, can be set at the distance close to the CCD 11, and the luminous intensity of each color can be improved.

According to the above, the light emission points of the light-emitting diodes 10R and 10R-1, the light emission points of the light-emitting diodes 10G and 10G-1, and the light emission points of the light-emitting diodes 10B and 10B-1 are almost identical for the CCD 11, and the light is viewed by emitting from the same point. Therefore, an endoscopic image with no uneven color can be obtained.

Embodiment 2

Figure 5:
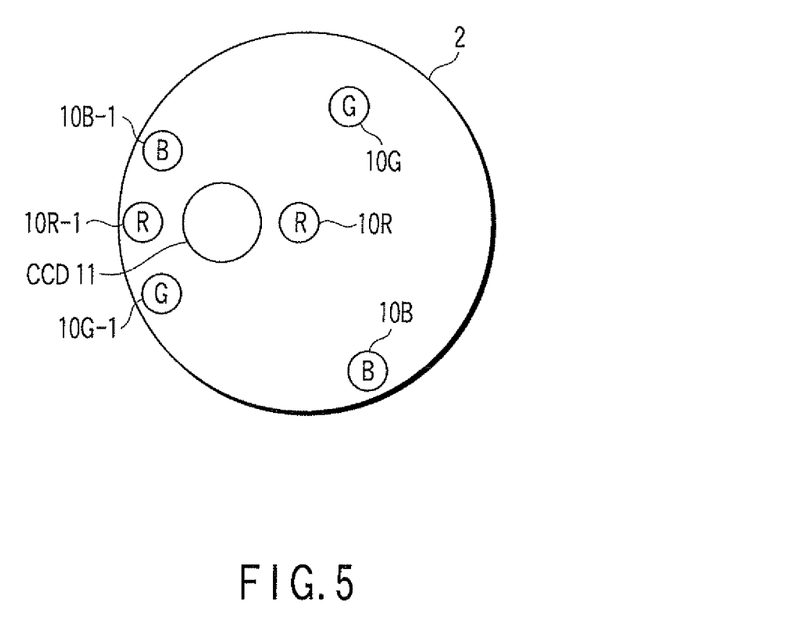
FIG. 5 is a view showing a modification of the first embodiment.
Figure 6:
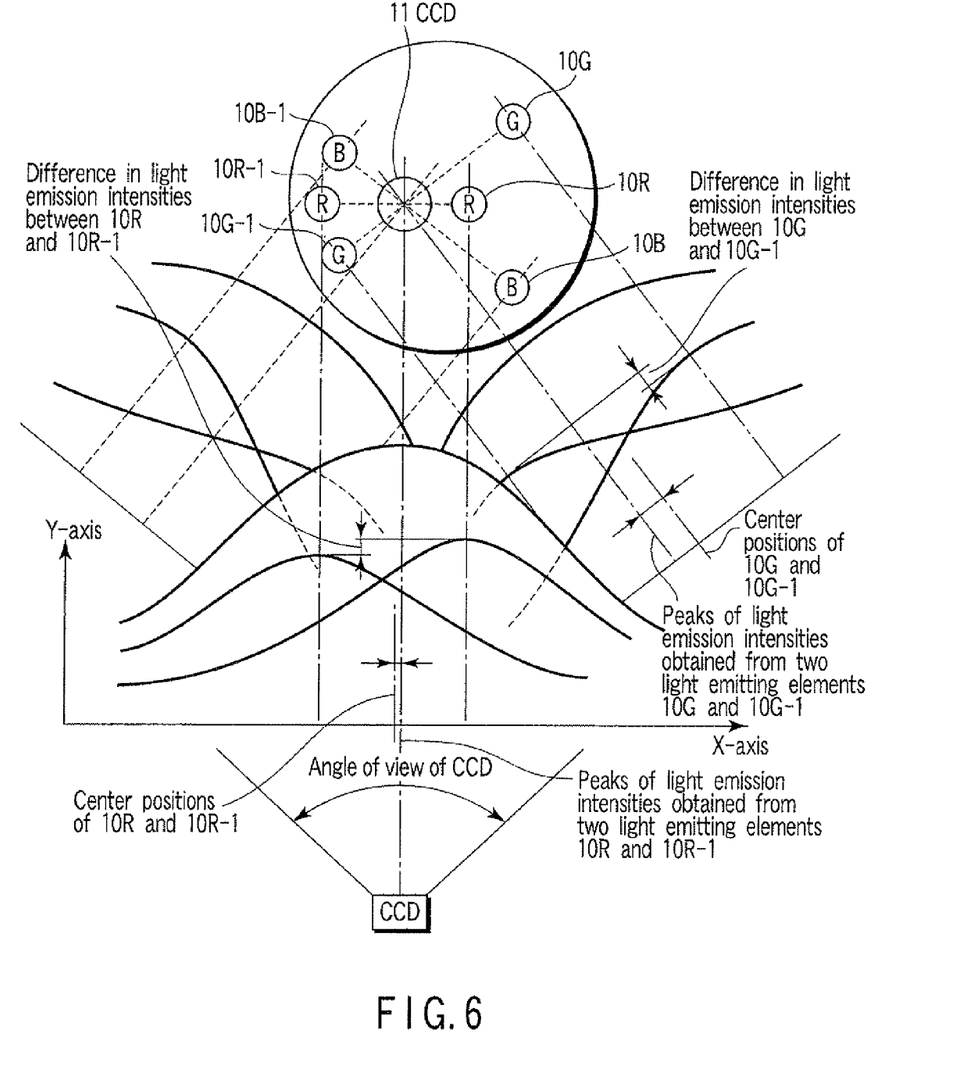
FIG. 6 is a view showing an example of control to make peaks of light from R/G/B light-emitting diodes almost identical in the angle of view of the CCD 11 in a second embodiment of the invention.

A second embodiment of the invention will be explained hereinafter. FIG. 5 is a view for explaining a problem that the first embodiment cannot solve, showing the case that R/G/B light-emitting diodes 10R, 10G and 10B are arranged asymmetrically to the CCD 11 due to the restrictions in the layout of distal end portion of an endoscope, for example. In such arrangement, the peaks of luminous intensity of light-emitting diodes 10R, 10G and 10B are not identical in the angle of view of CCD 11, and the problem of uneven color occurred in an endoscope image cannot actually be solved. Therefore, in this second embodiment, the arrangement of the light-emitting diodes 10R, 10G and 10B are not changed, but the light emission intensities of the light-emitting diodes 10R, 10G and 10B are changed, and the luminous intensity peaks of the R/G/B light-emitting diodes 10R and 10R-1, 10G and 10G-1, and 10B and 10B-1 are controlled to become almost identical in the angle of view of CCD 11, as shown in FIG. 6. The light emission intensity (light emission amount) of each light-emitting element may be controlled by correlating to the other light-emitting elements, and may be controlled independently of each other.

Therefore, the light emission points of the light-emitting diodes 10R and 10R-1, 10G and 10G-1, and 10B and 10B-1 become almost identical with respect to the CCD 11, and the light is viewed by lighting from the same point. Therefore, an endoscopic image with no uneven color can be obtained.

In the above-mentioned second embodiment, two pairs of R/G/B light-emitting diodes are arranged so as to surround the CCD 11. However, three or more pairs of light-emitting diodes may be arranged so as to surround the CCD 11.

Figure 7:
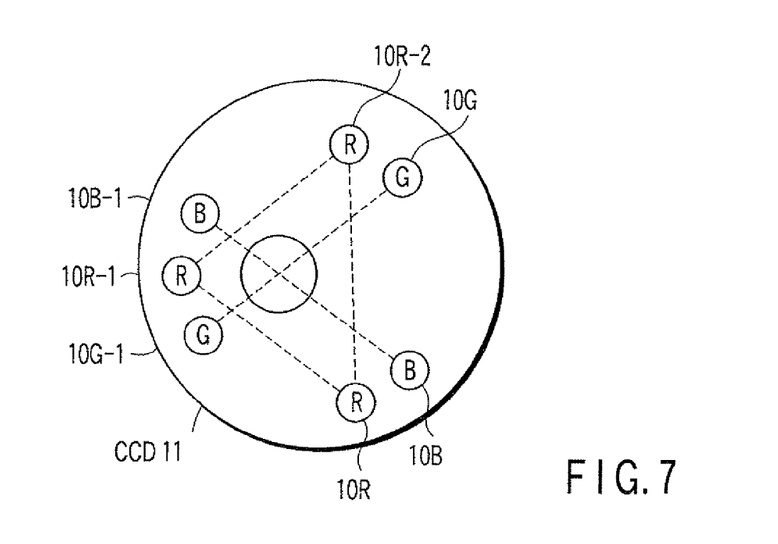
FIG. 7 is a view showing an example wherein three R light-emitting diodes are arranged in the second embodiment of the invention.

FIG. 7 is a view showing an example that three or more (three, 10R, 10R-1 and 10R-2R in FIG. 7) light-emitting diodes are arranged. In this example, the light-emitting diodes 10R and 10R-1 and 10R and 10R-2 are arranged so as to surround the CCD 11. Three or more G/B light-emitting diodes may be used in the similar method of arrangement.

Embodiment 3

Figure 8:
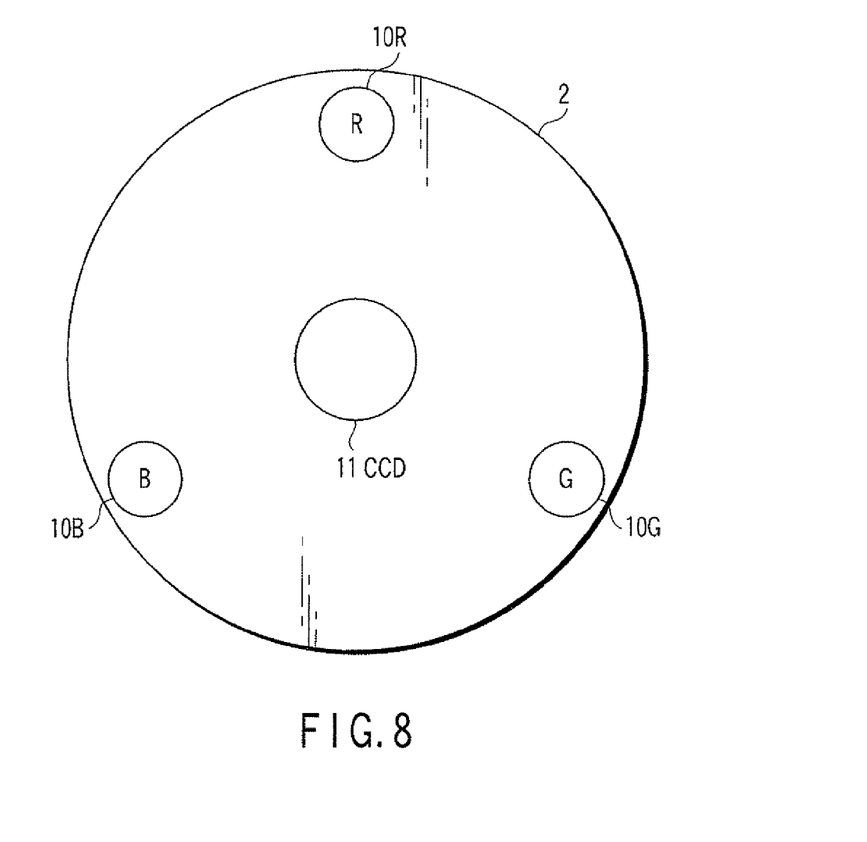
FIG. 8 is a view for explaining a problem in conventional arrangement, in a third embodiment of the invention.

A third embodiment of the invention will be explained hereinafter. In the third embodiment, a CCD is arranged at the center of a distal end portion. FIG. 8 is a view for explaining a problem in conventional arrangement. When the light-emitting diodes 10R, 10G and 10B are lit in such arrangement, as the light emission points of the light-emitting diodes 10R, 10G and 10B are different for the CCD 11, the luminous intensity peaks of the light-emitting diodes 10R, 10G and 10B do not become identical in the angle of view of the CCD 11, and uneven color occurs in an endoscopic image.

Figure 9A:
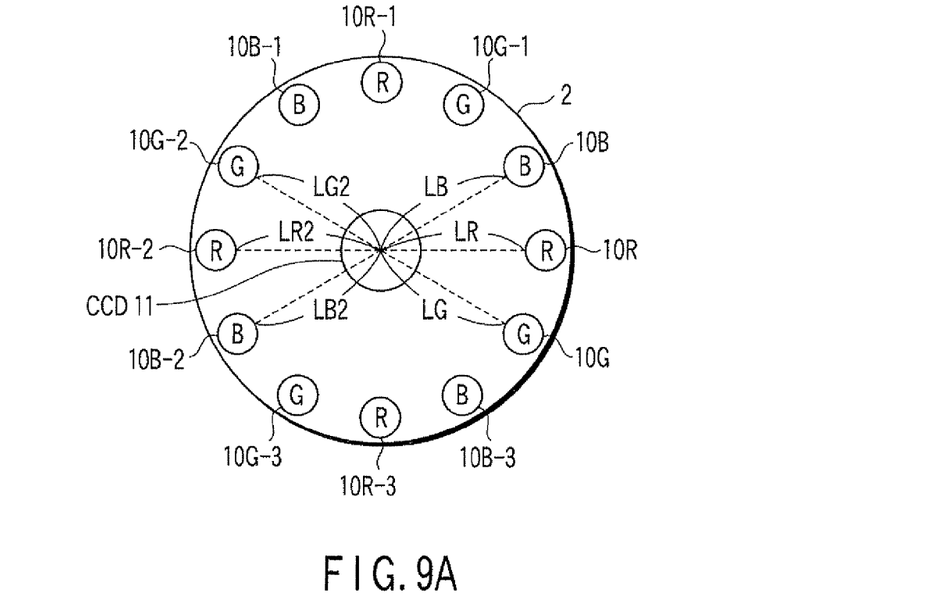
FIG. 9A is a view showing arrangement in a distal end portion of an endoscope according to a third embodiment of the invention.

FIG. 9A shows the configuration of a distal end portion of an endoscope according to a third embodiment. Here, the light-emitting diodes 10R, 10G and 10B are arranged at the positions substantially of point symmetry with respect to the CCD 11, thereby surrounding the CCD 11. Three pairs of R/G/B light-emitting diodes 10R-1, 10G-1, 10B-1, 10R-2, 10G-2, 10B-2, 10R-3, 10G-3 and 10B-3 are also arranged at the positions that surround the CCD 11. Here, four R/G/B light-emitting elements are arranged, but two or more one-color light-emitting elements may be arranged. However, when two light-emitting elements are used, they shall be arranged at positions that substantially surround the CCD 11.

Hereinafter, explanation will be give on the light-emitting diodes 10R, 10G, 10B, and their opposite light-emitting diodes 10R-2, 10G-2 and 10B-2. This is the same as for the other light-emitting diodes opposite to each other.

Figure 9B:
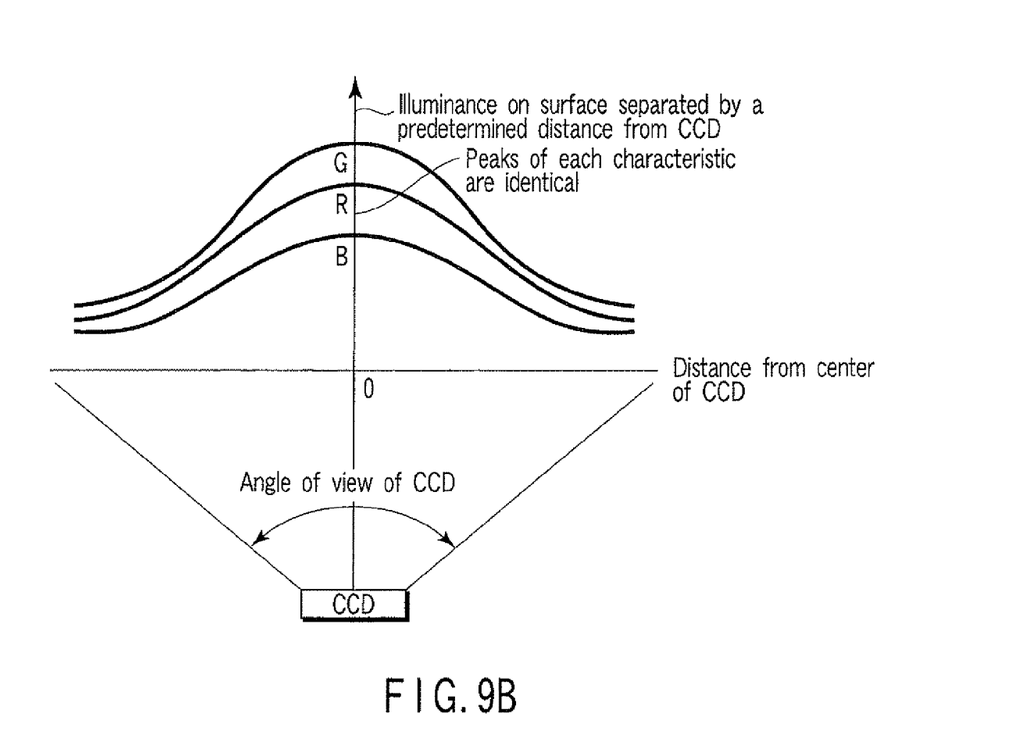
FIG. 9B is a view showing light intensity distribution in the arrangement in the distal end portion of the endoscope shown in FIG. 9A.

By adjusting the light emission intensity according to the distances LR and LR2 from the center of CCD 11 to the light-emitting diodes 10R and 10R-2, the distances LG and LG2 from the center of CCD 11 to the light-emitting diode 10G and 10G-2, and the distances LB and LB2 from the center of CCD 11 to the light-emitting diode 10B and 10B-2, the luminous intensity peak when lighting the light-emitting diodes 10R and 10R-2, the luminous intensity peak when lighting the light-emitting diodes 10G and 10G-2, and the luminous intensity peak when lighting the light-emitting diodes 10B and 10B-2 can be made almost identical in the angle of view of CCD 11. In this case, the light emission intensities in the above three luminous intensity distributions have peaks at the center of CCD 11.

Therefore, the light emission points of the light-emitting diodes 10R and 1R-2, 10G and 10G-2, and 10B and 10B-2 become almost identical with respect to the CCD 11, and the light is viewed by lighting from the same point. Therefore, an endoscopic image with no uneven color can be obtained.

In the above-mentioned third embodiment, four pairs of R/G/B light-emitting diodes are arranged to be symmetrical to the CCD 11, but five or more pairs of light-emitting diodes may be arranged to be symmetrical to the CCD 11.

In the above-mentioned third embodiment, the CCD is arranged at the center of the distal end portion, but as the luminous intensity peak can be shifted by adjusting the light emission intensity, it is obvious that each color is viewed by emitting from the same point, even if the CCD is arranged at a position out of the center of the distal end portion.

Further, in this embodiment, a light-emitting element as a lighting means is a light-emitting diode, but a laser diode may be used. A CCD is used as an image pickup element, but a CMOS may be used. Three sets of light-emitting diode driving controller 3 are separately arranged, but they may be arranged in the video processor 4, in the distal end of the electronic endoscope 2, or in a not-shown operation unit in the electronic endoscope 2.

According to the invention, there is provided a light source apparatus capable of providing endoscopic images without uneven color.

What is claimed is:

1. A light source apparatus comprising:
   a plurality of first light-emitting elements which emit a first illumination light including a light with a first wavelength to be applied to a subject, and which are located in a position at a first distance from an image-pickup element; and a plurality of second light-emitting elements which emit at least a second illumination light including a light with a second wavelength that is different from the first wavelength of the light included in the first illumination light emitted from the first light-emitting elements, and which are located in a position at a second distance, different from the first distance, from the image-pickup element, wherein the respective light-emitting elements have light emission intensities that vary so that a peak portion of a first light emission intensity obtained by combining the first illumination lights emitted from the plurality of first light-emitting elements in a direction parallel to a surface direction, in which the plurality of first light-emitting elements and the plurality of second light-emitting elements are arranged, coincides with a peak portion of a second light emission intensity obtained by combining the second illumination lights emitted from the plurality of second light-emitting elements in a direction parallel to the surface direction in an angle of view of the image pickup element.

2. The light source apparatus of claim 1, wherein the plurality of first light-emitting elements and the plurality of second light-emitting elements are arranged and emit light so that the peak portion of the first light emission intensity and the peak portion of the second light emission intensity coincide with a center of the image pickup element which picks up the image of the subject.

3. A light source apparatus comprising:
a plurality of first light-emitting elements which emit a first illumination light including a light with a first wavelength to be applied to a subject, and which are located in a position at a first distance from an image-pickup element; and
a plurality of second light-emitting elements which emit at least a second illumination light including a light with a second wavelength that is different from the first wavelength of the light included in the first illumination light emitted from the first light-emitting elements, and which are located in a position at a second distance, different from the first distance, from the image-pickup element which picks up an image of the subject on a plane identical to that of the plurality of first light-emitting elements, wherein the respective light-emitting elements have light emission intensities that vary so that a peak portion of a first light emission intensity obtained by combining the first illumination lights emitted from the plurality of first light-emitting elements in a direction parallel to a surface direction, in which the plurality of first light-emitting elements and the plurality of second light-emitting elements are arranged, coincides with a peak portion of a second light emission intensity obtained by combining the second illumination lights emitted from the plurality of second light-emitting elements in a direction parallel to the surface direction in a position on the plane.

4. The light source apparatus of claim 3, wherein the plurality of first light-emitting elements and the plurality of second light-emitting elements are arranged and emit light so that the peak portion of the first light emission intensity and the peak portion of the second light emission intensity coincide with a center of the image pickup element which picks up the image of the subject.

5. A light source apparatus comprising:
a plurality of first light-emitting elements which emit a first illumination light including a light with a first wavelength to be applied to a subject;
a plurality of second light-emitting elements which emit at least a second illumination light including a light with a second wavelength that is different from the first wavelength of the light included in the first illumination light emitted from the first light-emitting elements; and
a control unit which controls amounts of lights emitted from the plurality of first light-emitting elements and the plurality of second light-emitting elements so that a peak portion of a first light emission intensity obtained by combining the first illumination lights emitted from the plurality of first light-emitting elements coincides with a peak portion of a second light emission intensity obtained by combining the second illumination lights emitted from the plurality of second light-emitting elements, wherein each of the plurality of first light-emitting elements and the plurality of second light-emitting elements has a plurality of peak portions in a direction parallel to a surface direction in which the light-emitting elements are arranged, and the plurality of first light-emitting elements and the plurality of second light-emitting elements are located in positions at different distances from an image-pickup element which picks up an image of the subject, and the control unit controls the amounts of lights emitted from the plurality of first light-emitting elements and the plurality of second light-emitting elements so that the peak portion of the first light emission intensity obtained by combining the first illumination lights emitted from the plurality of first light-emitting elements coincides with the peak portion of the second light emission intensity obtained by combining the second illumination lights emitted from the plurality of second light-emitting elements in an angle of view of the image pickup element.

6. The light source apparatus of claim 5, wherein the control unit performs one of control of adjusting an amount of light of one light-emitting element in association with an amount of light of another light emitting element and control of independently adjusting an amount of light of one light-emitting element and an amount of light of another light-emitting element.

* * * * *